US006699691B2

(12) United States Patent
Inan et al.

(10) Patent No.: US 6,699,691 B2
(45) Date of Patent: Mar. 2, 2004

(54) ALCOHOL OXIDASE 1 REGULATORY NUCLEOTIDE SEQUENCES FOR HETEROLOGOUS GENE EXPRESSION IN YEAST

(75) Inventors: Mehmet Inan, Lincoln, NE (US); Michael M. Meagher, Lincoln, NE (US); Andrew K. Benson, Lincoln, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 10/116,993

(22) Filed: Apr. 5, 2002

(65) Prior Publication Data

US 2003/0044947 A1 Mar. 6, 2003

Related U.S. Application Data

(60) Provisional application No. 60/281,861, filed on Apr. 5, 2001.

(51) Int. Cl.[7] .......................... C12P 21/02; C12N 1/00; C12N 1/15; C12N 5/10; C12N 15/11; C12N 15/63
(52) U.S. Cl. ................... 435/69.1; 435/243; 435/254.2; 435/255.4; 435/255.5; 435/255.6; 435/320.1; 435/325; 435/419; 536/24.1
(58) Field of Search ..................... 536/24.1; 435/320.1, 435/325, 419, 243, 69.1

(56) References Cited

U.S. PATENT DOCUMENTS

| | | | |
|---|---|---|---|
| 4,703,004 A | 10/1987 | Hopp et al. | |
| 4,782,137 A | 11/1988 | Hopp et al. | |
| 4,855,231 A | 8/1989 | Stroman et al. | |
| 5,032,516 A | 7/1991 | Cregg | |
| 5,166,329 A | 11/1992 | Cregg | |
| 5,500,483 A | 3/1996 | Kumagai et al. | |
| 5,594,115 A | 1/1997 | Sharma | |
| 5,641,661 A | 6/1997 | Kumagai et al. | |
| 5,935,824 A | 8/1999 | Sgarlato | |
| 6,033,898 A | 3/2000 | Sarthy et al. | |

FOREIGN PATENT DOCUMENTS

| | | | |
|---|---|---|---|
| EP | 0 226 752 A1 | | 7/1987 |
| EP | 0244598 | * | 11/1987 |
| EP | 0 483 115 A2 | | 4/1992 |
| EP | 0 560 401 A1 | | 9/1993 |
| WO | WO 97/12044 | | 4/1997 |

OTHER PUBLICATIONS

Ellis, et al., "Isolation of Alcohol Oxidase and Two Other Methanol Regulatable Genes from the Yeast *Pichia pastoris*", Molecular and Collular Biology, Salk Insistute, vol. 5, pp. 1111–1121 (1985).

Altschul et al., "Basic Local Alignment Search Tool." Journal of Molecular Biology, 1990, pp. 403–410, vol. 215, No. 3.
Birren et al., "Sequence Analysis, A Laboratory Manual." Genome Analysis, 1997, pp. 543–559, vol. 1, Cold Spring Harbor Laboratory Press.
Carrillo et al., "The Multiple Sequence Alignment Problem in Biology." Siam Journal on Applied Mathematics, 1988, pp. 1073–1082, vol. 48, No. 5.
Coulson A., "High Performance Searching of Biosequence Database." Trends in Biotechnology, 1994, pp. 76–80, vol. 12, No. 3(122).
Cregg et al., "Functional Characterization of Two Alcohol Oxidase Genes from the Yeast *Pichia pastoris*." Molecular and Cellular Biology, 1989, pp. 1316–1323, vol. 9, No. 3.
Cregg et al., "Recombinant Protein Expression in *Pichia pastoris*." Molecular Biotechnology, 2000, pp. 23–52, vol. 16, No. 1.
Cregg et al., "Recent Advances in the Expression of Foreign Genes in *Pichia pastoris*." Biotechnology, 1993, pp. 905–910, vol. 11, No. 8.
Devereux et al., "A Comprehensive set of Sequence Analysis Programs for the VAX." Nucleic Acids Research, 1984, pp. 387–395, vol. 12, No. 1.
Guarente et al., "Fusion of *Escherichia coli* lacZ to Cytochrome c gene of *Saccharomyces cervevisiae*." Proceedings of the National Academy of Sciences of the USA, 1981, pp. 2199–2203, vol. 78, No. 4.
Koutz et al., "Structural Comparison of the *Pichia pastoris* Alcohol Oxidase Genes." Yeast, 1989, pp. 167–177, vol. 5, No. 3.
Ohi et al., "The Positive and Negative cis–acting Elements for Methanol Regulation in the *Pichia pastoris AOX2* gene." Mol. Gen. Genet, 1994, pp. 489–499, vol. 243, No. 5.
Miller J.H. (ed), "Experiment 48, Assay of β–Galactosidase." Experiments in Molecular Genetic, Cold Spring Harbor Laboratory, 1972, pp. 352–355.
Sears et al., "A Versatile Set of Vectors for Constitutive and Regulated Gene Expression in *Pichia pastoris*." Yeast, 1998, pp. 783–790, vol. 14, No. 5.
Meinkoth et al., "Hybridization of Nucleic Acids Immobilized on Solid Supports." Analytical Biochemistry, 1984, pp. 267–284, vol. 138, No. 1.
Tschopp et al., "Expression of lacZ gene from two Methanol–regulated Promoters in *Pichia pastoris*." Nucleic Acids Research, 1987, pp. 3859–3877, vol. 15, No. 9.

* cited by examiner

Primary Examiner—Terry McKelvey
(74) Attorney, Agent, or Firm—Scully, Scott, Murphy & Presser

(57) ABSTRACT

Polynucleotides that comprise regulatory regions of the yeast alcohol oxidase 1 promoter are provided. Isolated polynucleotides, recombinant polynucleotides, vectors, expression cassettes and transformed cells containing the regulatory regions are disclosed. Proteins produced by the transformed cells are also provided.

20 Claims, 6 Drawing Sheets

|  | | β-GAL Assay | |
|---|---|---|---|
| | | MM | MME |
| pAL2 | -1052 (A-F) | 100 | 3.1±0.3 |
| pAL132 | -800 | 76±5 | 1.9±0.2 |
| pAL285 | -658 | 49±4 | 2.2±0.5 |
| pAL424 | -518 | 14±3 | 1.3±0 |
| pAL551 | -390 | 24±7 | 1.8±0 |
| pAL669 | -239 | 7±2 | 1.8±0.2 |
| pALD1 | -797 / -658 | 63±3 | 2.1±0.2 |
| pALD2 | -656 / -518 | 109±12 | 3.8±0.4 |
| pALD3 | -517 / -390 | 128±6 | 5.0±0.6 |
| pALD4 | -390 / -239 | 16±1 | 0.8±0.2 |

| Pos | +/- | Sequence | Fragment | | |
|---|---|---|---|---|---|
| -726 | + | gctcaTTCCAAttcct | A | Seq. ID No. 6 |
| -519 | - | ctgtcTTGGAAcctaa | C | Seq. ID No. 7 |
| -428 | + | gaaacTTCCAAaagtc | C | Seq. ID No. 8 |
| -245 | + | tatgcTTCCAAgattc | E | Seq. ID No. 9 |
| -79 | + | actggTTCCAAttgac | F | Seq. ID No. 10 |

B

| -677 | - | cctgtCTATCctggc | B | Seq. ID No. 11 |
|---|---|---|---|---|
| -340 | - | tctctCTATCgcttc | D | Seq. ID No. 12 |
| -218 | + | ctgctGATAGcctaa | E | Seq. ID No. 13 |

C

```
Moxuas2        GAGTTCGAGGTCGTG
AOX1p  -583    GAGTGTGGGGTCAAA          C      Seq. ID No. 14
Consensus gagt  g  ggtc                        Seq. ID No. 15
```

FIGURE 6

ALCOHOL OXIDASE 1 REGULATORY NUCLEOTIDE SEQUENCES FOR HETEROLOGOUS GENE EXPRESSION IN YEAST

FIELD OF THE INVENTION

The current invention is generally directed toward isolated polynucleotides comprising regulatory nucleotide sequences, vectors and expression cassettes containing such regulatory sequences, and host cells comprising the vectors and/or expression cassettes. In particular, the invention relates to 5' upstream regulatory nucleotide sequences within the promoter region of the alcohol oxidase 1 gene, vectors and expression cassettes containing such regulatory sequences, and host cells comprising the vectors and/or expression cassettes.

BACKGROUND OF THE INVENTION

Methylotrophic yeast are capable of utilizing methanol as their sole energy source. The methylotrophic yeast comprise two groups, the asporagenous consisting of the Candida and Torulopsis species, and the ascomycetous consisting of the Hansenula and Pichia species. These yeast possess a conserved methanol utilization pathway. In the first step of this pathway, the enzyme alcohol oxidase catalyzes the oxidation of methanol to formaldehyde. Concomitantly, this reaction also generates hydrogen peroxide, a substance that is highly toxic to most cellular organelles. In order to avoid hydrogen peroxide toxicity, methanol metabolism is highly compartmentalized in specialized organelles, called peroxisomes, which sequester this toxic byproduct from the rest of the cell. Alcohol oxidase has a low affinity for its substrate, oxygen. The partitioning of alcohol oxidase in the peroxisome, therefore, serves the additional role of concentrating the enzyme and substrate, thereby compensating, at least in part, for its low oxygen affinity.

The regulation of methanol metabolism in yeast generally occurs at the level of transcription, and includes control of the synthesis and activation of corresponding enzymes, as well as their degradation. Synthesis of methanol metabolizing enzymes is induced by methanol, formaldehyde and formate, and repressed by both glucose and ethanol. As stated above, a key enzyme in methanol oxidation is alcohol oxidase, which is also controlled both positively and negatively at the transcription level. Several genes encoding alcohol oxidase from *Pichia pastoris* (AOX1 and AOX2), *Candida boidinii* S2 (AOD1), and methanol oxidase from *Hansenula polymorpha* (MOX1) are well characterized. Methanol induction causes the rapid de novo synthesis of alcohol oxidase, which is accompanied by a corresponding increase in alcohol oxidase mRNA. For example, in methanol grown *P. pastoris* cells, AOX rapidly accumulates up to 30% of the total soluble protein.

Yeasts have been extensively employed for the production of heterologous proteins and offer several advantages over prokaryotic expression systems. For example, some eukaryotic proteins that are produced in prokaryotic cells are either unstable or lack biological activity. Accordingly, in these cases, yeasts offer advantages over their prokaryotic counterparts which include an intracellular environment that is more conducive for correct folding of eukaryotic proteins. Additionally yeasts, unlike prokaryotic hosts, have the ability to glycosylate proteins, which is important for both the stability and biological activity of the protein.

*Saccharomyces cerevisiae* was the first, and remains the most commonly employed eukaryotic expression system because its genome and physiology have been extensively characterized. It is not always the optimal expression system, however, for the large-scale production of heterologous proteins because of plasmid loss during scale-up, hyperglycosylation, and low protein yields. Recently, methylotrophic yeast expression systems have been developed and offer several advantages over their counterpart, *S. cerevisiae*. For example, methylotrophic yeast expression systems achieve very high cell densities in a simple defined medium, have strong inducible promoters, and the availability of methods, host strains, and expression vectors that facilitate genetic manipulations.

In particular, the methylotrophic yeast, *P. pastoris*, has been extensively utilized for the production of heterologous proteins at the industrial scale. *P. pastoris* is a particularly suitable expression system for the production of proteins at the industrial scale because of the presence of a unique promoter, AOX1, used to drive gene expression. The AOX1 promoter, as stated above, is derived from the methanol regulated alcohol oxidase I gene and is one of the most efficient and tightly regulated promoters known. For example, as delineated above, in methanol grown *P. pastoris* cells, AOX rapidly accumulates up to 30% of the total soluble protein.

In addition to the AOX1 gene, *P. pastoris* also harbors a second functional AOX gene, AOX2. AOX2 encodes a protein that shares approximately 97% homology, and has the same specific activity as its AOX1 counterpart. However, the 5' upstream regulatory regions of AOX1 and AOX2 do not have significant regions of homology, despite the fact that both genes are repressed during growth on glucose, derepressed during carbon limitation, and induced by growth on methanol as the sole carbon source. In addition, AOX2 induction is responsible for only 15% of total alcohol oxidase activity in methanol-grown cell cultures. Due to the limited accumulation of AOX2 relative to AOX1, the AOX1 promoter is more advantageous to employ in an expression system for large-scale protein production.

Although high-level expression of heterologous proteins has been achieved employing the AOX1 promoter from *P. pastoris*, very little is known about the molecular mechanisms involved in methanol induction, either in *P. pastoris* or methylotrophic yeasts in general. The promoter region for AOX1 has been identified (SEQ ID NO: 1), however, regulatory sequences within this region have not been extensively characterized. See Stroman et al., U.S. Pat. No. 4,855,231. In addition, the promoter region for the AOX2 gene has also been identified (SEQ ID NO: 2), and consists of three cis-acting regulatory elements that have been characterized (one positive and the other two negative). See Cregg., U.S. Pat. No. 5,032,516. The positive cis-acting element, the AOX2 upstream activator site, is required for a response to transcriptional induction by methanol. The two negative cis-acting elements are responsible for repression of the AOX2 promoter. However, as delineated above, the 5' upstream regulatory regions of AOX1 and AOX2 do not have significant regions of homology and thus, the extensive characterization of AOX2 regulation provides little insight into the mechanism by which the AOX1 promoter is regulated.

In yet a further attempt to characterize regulatory regions of the AOX1 promoter, its sequence was compared to the 5' upstream regulatory regions of an alcohol oxidase gene, ZZA (SEQ ID NO: 3), isolated from an uncharacterized *P. pastoris* strain. See Kumagai et al., U.S. Pat. No. 5,641, 661. This strain also contains two copies of the AOX genes. The deduced amino acid sequence of ZZA revealed that 14 of the first 16 amino acids are identical to that of the AOX1 and AOX2 genes. However, similar to the 5' regulatory regions of AOX1 and AOX2, the 5' upstream regulatory regions of ZZA and AOX1 share only 66% homology. The two promoters, thus, may be regulated by completely distinct mechanisms.

Highly conserved nucleotide sequences, (TTGNNNGCTTCCAANNNTGGT) (SEQ ID NO: 4) and CCNCTTTTTG (SEQ ID NO: 5) have been found in the 5' flanking regions of alcohol oxidase, methanol oxidase, and dihydroxyacetone synthase genes in P. pastoris, H. polymorpha and C. boidini S2. See Kumagai et al., U.S. Pat. No. 5,641,661. It was postulated that these conserved regions were involved in binding methanol-specific trans-acting factors. However, in a study characterizing the AOX2 promoter, these sequences were not involved in transcriptional regulation of the AOX2 gene since deletion of these regions did not impact regulation of the AOX2 promoter (Ohi, et al. (1994) Mol.Gen Genet 243:489–99). Thus, although these regions may be highly conserved across methylotrophic yeasts, their impact on transcriptional regulation of the AOX genes remains to be fully elucidated.

Accordingly, a need exists to identify promoters and other regulatory nucleotide sequences for the controlled expression and/or high level expression of heterologous proteins in yeast. In particular, a need exists to provide new AOX1 promoters and regulatory nucleotide sequences for the controlled expression and/or high level expression of heterologous proteins in yeast.

SUMMARY OF THE INVENTION

Among the several aspects of the invention therefore is provided an isolated polynucleotide comprising a regulatory region containing a nucleotide sequence less than about 1000 nucleotides long selected from the group consisting of:
(a) SEQ ID NO: 16, a fragment of SEQ ID NO: 16, the complement of SEQ ID NO: 16, or a fragment of the complement of SEQ ID NO: 16;
(b) a polynucleotide that hybridizes to the polynucleotide of (a) under conditions of high stringency; and
(c) a polynucleotide with at least 80% sequence homology to the polynucleotide of (a).

Another aspect provides an isolated polynucleotide comprising a regulatory region containing a nucleotide sequence less than about 1000 nucleotides long selected from the group consisting of:
(a) SEQ ID NO: 17, a fragment of SEQ ID NO: 17, the complement of SEQ ID NO: 17, or a fragment of the complement of SEQ ID NO: 17;
(b) a polynucleotide that hybridizes to the polynucleotide of (a) under conditions of high stringency; and
(c) a polynucleotide with at least 80% sequence homology to the polynucleotide of (a).

In yet another aspect is provided an isolated polynucleotide comprising a regulatory region containing a nucleotide sequence less than about 1000 nucleotides long selected from the group consisting of:
(a) SEQ ID NO: 18, a fragment of SEQ ID NO: 18, the complement of SEQ ID NO: 18, or a fragment of the complement of SEQ ID NO: 18;
(b) a polynucleotide that hybridizes to the polynucleotide of (a) under conditions of high stringency; and
(c) a polynucleotide with at least 80% sequence homology to the polynucleotide of (a).

Still another aspect of the invention is provided an isolated polynucleotide comprising a regulatory region containing a nucleotide sequence less than about 1000 nucleotides long selected from the group consisting of:
(a) SEQ ID NO: 19, a fragment of SEQ ID NO: 19, the complement of SEQ ID NO: 19, or a fragment of the complement of SEQ ID NO: 19;
(b) a polynucleotide that hybridizes to the polynucleotide of (a) under conditions of high stringency; and
(c) a polynucleotide with at least 80% sequence homology to the polynucleotide of (a).

In yet a further aspect of the invention is provided an isolated polynucleotide comprising a regulatory region containing a nucleotide sequence less than about 1000 nucleotides long selected from the group consisting of:
(a) SEQ ID NO: 20, a fragment of SEQ ID NO: 20, the complement of SEQ ID NO: 20, or a fragment of the complement of SEQ ID NO: 20;
(b) a polynucleotide that hybridizes to the polynucleotide of (a) under conditions of high stringency; and
(c) a polynucleotide with at least 80% sequence homology to the polynucleotide of (a).

A further aspect of the invention provides an isolated polynucleotide comprising a regulatory region containing a nucleotide sequence less than about 1000 nucleotides long selected from the group consisting of:
(a) SEQ ID NO: 21, a fragment of SEQ ID NO: 21, the complement of SEQ ID NO: 21, or a fragment of the complement of SEQ ID NO: 21;
(b) a polynucleotide that hybridizes to the polynucleotide of (a) under conditions of high stringency; and
(c) a polynucleotide with at least 80% sequence homology to the polynucleotide of (a).

Still another aspect of the invention provides a recombinant vector comprising the polynucleotide of SEQ ID NO: 16, SEQ ID NO: 17, SEQ ID NO: 18, SEQ ID NO: 19, SEQ ID NO: 20, and SEQ ID NO: 21. Host cells comprising the recombinant vector are also provided.

A further aspect provides an expression cassette comprising the polynucleotide of SEQ ID NO: 16, SEQ ID NO: 17, SEQ ID NO: 18, SEQ ID NO: 19, SEQ ID NO: 20, and SEQ ID NO: 21. Host cells comprising the expression cassette are also provided.

BRIEF DESCRIPTION OF THE DRAWINGS

These and other features, aspects, and advantages of the present invention will become better understood with regard to the following description, appended claims, and accompanying figures where:

FIG. 2 depicts deletion analysis of the AOX1 promoter. The plasmids were inserted into GS115 his4 locus. Single copy integrands were identified by Southern assay using HIS4 gene as a probe. The cells were grown in MM (induced) and MME (repressed) conditions. β-Gal activity of the AOX1-lacZ fusion was measured and reported as percent of activity of methanol-grown cells containing pAL2. The TATA box is indicated by the black square, and +1 ATG is indicated by the upside down, black triangle.

FIG. 6 depicts the consensus sequences of methanol regulated promoters of methylotrophic yeast. Occurrence of TTCCAA (A) (Kumagai et al., 1993) and GATAG (B) (Ohi et al., 1994) core consensus sequence in AOX1 promoter. C, Alignment of the MOX UAS2 with AOX1 promoter (Godecke et al., 1994). Minus numbers are given relative to +1 ATG codon, +/− defines plus/minus strand. The fragment letters containing the sequences are also given in the right column.

ABBREVIATIONS AND DEFINITIONS

Figure 1:
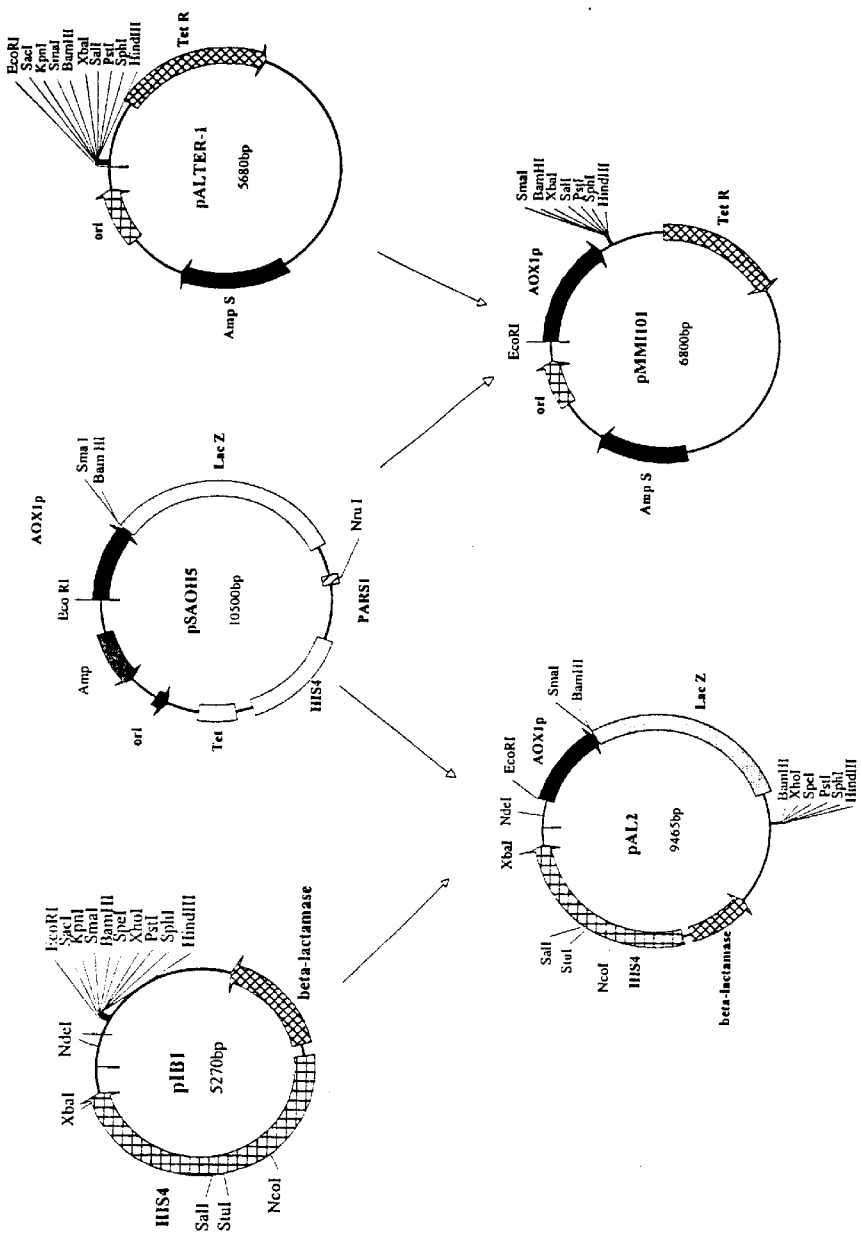
FIG. 1 depicts the construction of expression vector, pAL2 and mutagenesis vector pMMI101. PAL2 was constructed by inserting Eco RI/Sma I fragment of pSAOH5 into pIB1 promoterless vector. The vector pMMI101 was constructed by inserting Eco RI/Bam HI fragment of pSAOH5 into Eco RI/Bam.

To facilitate understanding of the invention, a number of terms and abbreviations as used herein are defined below:

As used herein "isolated polynucleotide" means a polynucleotide that is free of one or both of the nucleotide sequences which flank the polynucleotide in the naturally-occurring genome of the organism from which the polynucleotide is derived. The term includes, for example, a polynucleotide or fragment thereof that is incorporated in a vector or expression cassette; into an autonomously replicating plasmid or virus; into the genomic DNA of a prokaryote or eukaryote; or that exists as a separate molecule independent of other polynucleotides. It also includes a recombinant chimeric polynucleotide that is part of a hybrid polynucleotide, for example, one encoding a polypeptide sequence.

As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications, for example, labels, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands.

As used herein, "sequence" means the linear order in which monomers occur in a polymer, for example, the order of amino acids in a polypeptide or the order of nucleotides in a polynucleotide.

As used herein, the terms "complementary" or "complementarity" refer to the pairing of bases, purines and pyrimidines, that associate through hydrogen bonding in double stranded nucleic acid. The following base pairs are complementary: guanine and cytosine; adenine and thymine; and adenine and uracil. The terms as used herein include complete and partial complementarity.

As used herein, the term "hybridization" refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Thus the term contemplates partial as well as complete hybridization. Such techniques and conditions are well known to practitioners in this field.

As used herein, "expression cassette" means a genetic module comprising a gene and the regulatory regions necessary for its expression, which may be incorporated into a vector.

As used herein, "secretion sequence" or "signal peptide" or "signal sequence" means a sequence that directs newly synthesized secretory or membrane proteins to and through membranes of the endoplasmic reticulum, or from the cytoplasm to the periplasm across the inner membrane of bacteria, or from the matrix of mitochondria into the inner space, or from the stroma of chloroplasts into the thylakoid. Fusion of such a sequence to a gene that is to be expressed in a heterologous host ensures secretion of the recombinant protein from the host cell.

As used herein, "operably linked" means any linkage, irrespective of orientation or distance, between a regulatory sequence and coding sequence, where the linkage permits the regulatory sequence to control expression of the coding sequence.

As used herein, "heterologous coding sequence" means any coding sequence other than the one that naturally encodes the alcohol oxidase 1 protein, or any homolog of the alcohol oxidase 1 protein.

As used herein, "regulatory sequence" or "regulatory region" as used in reference to a specific gene refers to the coding or non-coding nucleotide sequences within that gene that are necessary or sufficient to provide for the regulated expression of the coding region of a gene. Thus, the term encompasses promoter sequences, regulatory protein binding sites, upstream activator sequences and the like. Specific nucleotides within a regulatory region may serve multiple functions. For example, a specific nucleotide may be part of a promoter and participate in the binding of a transcriptional activator protein.

As used herein, "coding region" refers to that portion of a gene which codes for a protein. The term "non-coding region" refers to that portion of a gene that is not a coding region.

DESCRIPTION OF THE PREFERRED EMBODIMENTS

Applicants have identified regulatory nucleotide sequences that are part of the non-coding region of the alcohol oxidase 1 ("AOX1") gene. The AOX1 gene encodes the enzyme alcohol oxidase 1, which catalyzes the oxidation of methanol to formaldehyde (as stated in more detail above). The AOX1 promoter, is an inducible promoter, and is primarily induced by methanol and carbon starvation, and repressed in response to glucose and ethanol. Although the AOX1 promoter has been identified (SEQ ID NO: 1), prior to applicants discovery, 5' regulatory nucleotide sequences within the promoter region had not been characterized. The regulatory regions discovered by applicants, as set-forth herein, may be employed to increase the expression of genes of interest in a variety of cells.

Figure 3:
FIG. 3 depicts results of the gel shift assay for fragment A (SEQ ID NO: 16). Lane 1, no protein added; lane 2–5, six mg protein from MM grown cells; lane 6, six mg protein from MME grown cells; lane 3, thirty fold cold specific DNA (fragment A (SEQ ID NO: 16)); lane 4, thirty fold cold fragment C (SEQ ID NO: 18); lane 5 thirty fold *L. monocytogeneses* DNA.
Figure 4:
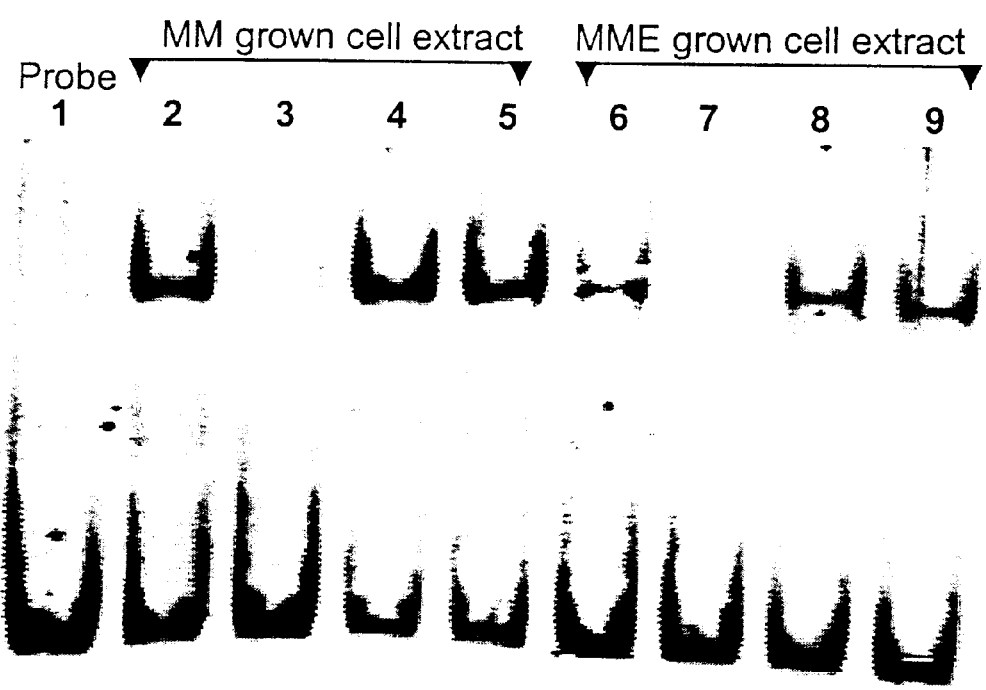
FIG. 4 depicts results of the gel shift assay for fragment C (SEQ ID NO: 18). Lane 1, no protein added; lanes 2–5, protein from MM grown cells; lanes 7–9, protein from MME grown cells; lane 3 and 7, thirty fold cold specific competitor (fragment C (SEQ ID NO: 18)); lanes 4 and 6, thirty fold cold unspecific competitor (fragment A (SEQ ID NO: 16)); lanes 5 and 9, thirty fold cold unspecific *L. monocytogenes* DNA.

In order to identify the regulatory regions of the present invention, applicants divided the 1052 base pair AOX1 promoter (SEQ ID NO: 1) into six fragments, A (SEQ ID NO: 16), B (SEQ ID NO: 17), C (SEQ ID NO: 18), D (SEQ ID NO: 19), E (SEQ ID NO: 20), and F (SEQ ID NO: 21). Through a series of systematic deletions comprising both sequential deletions and dropout mutations, in conjunction with gel shift assays, regions of the AOX1 promoter (SEQ ID NO: 1) element involved in regulation and DNA-protein interactions were identified (as set-forth in more detail in the example section below). Based upon this deletion analysis, as depicted in FIG. 2, fragments A (SEQ ID NO: 16), B (SEQ ID NO: 17), C (SEQ ID NO: 18), E (SEQ ID NO: 20), and F (SEQ ID NO: 21) contain positive regulatory sites, while fragment D (SEQ ID NO: 19) contains a negative regulatory site. In addition, based upon gel shift assays, as depicted in FIG. 3 and FIG. 4, it is believed that fragments A (SEQ ID NO: 16), and C (SEQ ID NO: 18) contain sequences for different DNA-binding proteins. It should be noted that, specific nucleotides within a regulatory region may serve multiple functions. For example, a specific nucleotide may be part of a promoter and participate in the binding of a transcriptional activator protein. Thus, while applicants believe that A (SEQ ID NO: 16), B (SEQ ID NO: 17), C (SEQ ID NO: 18), E (SEQ ID NO: 20), and F (SEQ ID NO: 21) contain positive regulatory sites, and fragment D (SEQ ID NO: 19) contains a negative regulatory site, in addition to the stated function, each of these regulatory regions may serve multiple regulatory functions.

The present invention, therefore, encompasses an isolated polynucleotide comprising a regulatory region containing SEQ ID NO: 16, a fragment of SEQ ID NO: 16, the complement of SEQ ID NO: 16, or a fragment of the complement of SEQ ID NO: 16. In one embodiment the polynucleotide (or the fragment, or the complement of either the polynucleotide or fragment) is less than about 1000 nucleotides long, in another embodiment the polynucleotide is between about 4 nucleotides to about 750 nucleotides long. More preferably, however, the polynucleotide is between about 250 nucleotides to about 750 nucleotides long. The fragments may be employed as probes for SEQ ID NO: 16 or related sequences. Also included are isolated polynucleotides that hybridize to SEQ ID NO: 16, or the complement of SEQ ID NO: 16 under conditions of high stringency. In one embodiment these polynucleotides are less than about 1000 nucleotides long, in another embodiment these polynucleotides are between about 4 nucleotides to about 750 nucleotides long. Such polynucleotides may be used as probes for SEQ ID NO: 16 or related sequences.

Still another embodiment provides an isolated polynucleotide comprising a regulatory region containing SEQ ID NO: 17, a fragment of SEQ ID NO: 17, the complement of SEQ ID NO: 17, or a fragment of the complement of SEQ ID NO: 17. In one embodiment the polynucleotide (or the fragment, or the complement of either the polynucleotide or fragment) is less than about 1000 nucleotides long, in another embodiment the polynucleotide is between about 4 nucleotides to about 750 nucleotides long. More preferably, however, the polynucleotide is between about 250 nucleotides to about 750 nucleotides long. The fragments may be employed as probes for SEQ ID NO: 17 or related sequences. Also included are isolated polynucleotides that hybridize to SEQ ID NO: 17, or the complement of SEQ ID NO: 17 under conditions of high stringency. In one embodiment these polynucleotides are less than about 1000 nucleotides long, in another embodiment these polynucleotides are between about 4 nucleotides to about 750 nucleotides long. Such polynucleotides may be used as probes for SEQ ID NO: 17 or related sequences.

In yet another embodiment, the invention encompasses an isolated polynucleotide comprising a regulatory region containing SEQ ID NO: 18, a fragment of SEQ ID NO: 18, the complement of SEQ ID NO: 18, or a fragment of the complement of SEQ ID NO: 18. In one embodiment the polynucleotide (or the fragment, or the complement of either the polynucleotide or fragment) is less than about 1000 nucleotides long, in another embodiment the polynucleotide is between about 4 nucleotides to about 750 nucleotides long. More preferably, however, the polynucleotide is between about 250 nucleotides to about 750 nucleotides long. The fragments may be employed as probes for SEQ ID NO: 18 or related sequences. Also included are isolated polynucleotides that hybridize to SEQ ID NO: 18, or the complement of SEQ ID NO: 18 under conditions of high stringency (as defined herein). In one embodiment these polynucleotides are less than about 1000 nucleotides long, in another embodiment these polynucleotides are between about 4 nucleotides to about 750 nucleotides. Such polynucleotides may be used as probes for SEQ ID NO: 18 or related sequences.

An additional embodiment provides an isolated polynucleotide comprising a regulatory region containing SEQ ID NO: 19, a fragment of SEQ ID NO: 19, the complement of SEQ ID NO: 19, or a fragment of the complement of SEQ ID NO: 19. In one embodiment the polynucleotide (or the fragment, or the complement of either the polynucleotide or fragment) is less than about 1000 nucleotides long, in another embodiment the polynucleotide is between about 4 nucleotides to about 750 nucleotides long. More preferably, however, the polynucleotide is between about 250 nucleotides to about 750 nucleotides long. The fragments may be employed as probes for SEQ ID NO: 19 or related sequences. Also included are isolated polynucleotides that hybridize to SEQ ID NO: 19, or the complement of SEQ ID NO: 19 under conditions of high stringency. In one embodiment these polynucleotides are less than about 1000 nucleotides long, in another embodiment these polynucleotides are between about 4 nucleotides to about 750 nucleotides. Such polynucleotides may be used as probes for SEQ ID NO: 19 or related sequences.

In yet another embodiment, the invention encompasses an isolated polynucleotide comprising a regulatory region containing SEQ ID NO: 20, a fragment of SEQ ID NO: 20, the complement of SEQ ID NO: 20, or a fragment of the complement of SEQ ID NO: 20. In one embodiment the polynucleotide (or the fragment, or the complement of either the polynucleotide or fragment) is less than about 1000 nucleotides long, in another embodiment the polynucleotide is between about 4 nucleotides to about 750 nucleotides long. More preferably, however, the polynucleotide is between about 250 nucleotides to about 750 nucleotides long. The fragments may be employed as probes for SEQ ID NO: 20 or related sequences. Also included are isolated polynucleotides that hybridize to SEQ ID NO: 20, or the complement of SEQ ID NO: 20 under conditions of high stringency. In one embodiment these polynucleotides are less than about 1000 nucleotides long, in another embodiment these polynucleotides are between about 4 nucleotides to about 750 nucleotides long. Such polynucleotides may be used as probes for SEQ ID NO: 20 or related sequences.

A further embodiment of the present invention provides an isolated polynucleotide comprising a regulatory region containing SEQ ID NO: 21, a fragment of SEQ ID NO: 21, the complement of SEQ ID NO: 21, or a fragment of the complement of SEQ ID NO: 21. In one embodiment the polynucleotide (or the fragment, or the complement of either the polynucleotide or fragment) is less than about 1000 nucleotides long, in another embodiment the polynucleotide is between about 4 nucleotides to about 750 nucleotides long. More preferably, however, the polynucleotide is between about 250 nucleotides to about 750 nucleotides long. The fragments may be employed as probes for SEQ ID NO: 21 or related sequences. Also included are isolated polynucleotides that hybridize to SEQ ID NO: 21, or the complement of SEQ ID NO: 21 under conditions of high stringency. In one embodiment these polynucleotides are less than about 1000 nucleotides long, in another embodiment these polynucleotides are between about 4 nucleotides to about 750 nucleotides long. Such polynucleotides may be used as probes for SEQ ID NO: 21 or related sequences.

As is well known in the art, stringency is related to the $T_m$ of the hybrid formed. The $T_m$ (melting temperature) of a nucleic acid hybrid is the temperature at which 50% of the bases are base-paired. For example, if one the partners in a hybrid is a short oligonucleotide of approximately 20 bases, 50% of the duplexes are typically strand separated at the $T_m$. In this case, the $T_m$ reflects a time-independent equilibrium that depends on the concentration of oligonucleotide. In contrast, if both strands are longer, the $T_m$ corresponds to a situation in which the strands are held together in structure possibly containing alternating duplex and denatured regions. In this case, the $T_m$ reflects an intramolecular equilibrium that is independent of time and polynucleotide concentration.

As is also well known in the art, $T_m$ is dependent on the composition of the polynucleotide (e.g. length, type of duplex, base composition, and extent of precise base pairing) and the composition of the solvent (e.g. salt concentration and the presence of denaturants such formamide). An equation for the calculation of $T_m$ can be found in Sambrook et al. (*Molecular Cloning*, 2nd ed., Cold Spring Harbor Press, 1989) and is:

$$T_m = 81.5°\text{ C.} - 16.6(\log_{10}[\text{Na}^+]) = 0.41(\%\text{ G+C}) - 0.63(\%\text{ formamide}) - 600/L).$$

Where L is the length of the hybrid in base pairs, the concentration of $\text{Na}^+$ is in the range of 0.01M to 0.4M and the G+C content is in the range of 30% to 75%. Equations for hybrids involving RNA can be found in the same reference. Alternative equations can be found in Davis et al., *Basic Methods in Molecular Biology*, 2nd ed., Appleton and Lange, 1994, Sec 6–8.

Methods for hybridization and washing are well known in the art and can be found in standard references in molecular biology such as those cited herein. In general, hybridizations are usually carried out in solutions of high ionic strength (6×SSC or 6×SSPE) at a temperature 20–25° C. below the $T_m$. High stringency wash conditions are often determined empirically in preliminary experiments, but usually involve a combination of salt and temperature that is approximately 12–20° C. below the $T_m$. One example of high stringency conditions is 1×SSC at 60° C. Another example of high stringency wash conditions is 0.1×SSPE, 0.1% SDS at 42° C. (Meinkoth and Wahl, *Anal. Biochem.*, 138:267–284, 1984). An example of even higher stringency wash conditions is 0.1×SSPE, 0.1% SDS at 50–65° C. In one preferred embodiment, high stringency washing is carried out under conditions of 1×SSC and 60° C.

In another embodiment, the present invention provides an isolated polynucleotide sequence with at least 80%, more preferably 90%, more preferably still 95%, even more preferably 97% and still more preferably 99% sequence homology to SEQ ID NO: 16, SEQ ID NO: 17, SEQ ID NO: 18, SEQ ID NO: 19, SEQ ID NO: 20, or SEQ ID NO 21 or the complement of SEQ ID NO: 16, SEQ ID NO: 17, SEQ ID NO: 18, SEQ ID NO: 19, SEQ ID NO: 20, or SEQ ID NO 21.

"Homology", as is well understood in the art, is a relationship between two or more polypeptide sequences or two or more polynucleotide sequences, as determined by comparing the sequences. In the art, "homology" also means the degree of sequence relatedness between polypeptide or polynucleotide sequences, as determined by the match between strings of such sequences. "Homology" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data*, Part I, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., *SIAM J Applied Math*, 48:1073 (1988). Methods to determine homology are designed to give the largest match between the sequences tested. Moreover, methods to determine homology are codified in publicly available programs. Computer programs which can be used to determine identity/homology between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403–410 (1990)). The well known Smith Waterman algorithm can also be used to determine homology.

The isolated polynucleotide comprising the regulatory region of the present invention, without being bound by any particular limitation, may comprise any combination of SEQ ID NO: 16, SEQ ID NO: 17, SEQ ID NO: 18, SEQ ID NO: 19, SEQ ID NO: 20, and SEQ ID NO: 21 or a fragment of any of these sequences. Additionally, the regulatory region may comprise any combination of the complement of SEQ ID NO: 16, SEQ ID NO: 17, SEQ ID NO: 18, SEQ ID NO: 19, SEQ ID NO: 20, and SEQ ID NO: 21 or a fragment of the complement of any of these sequences. The regulatory region, may also comprise any combination of isolated polynucleotides that hybridize under conditions of high stringency to SEQ ID NO: 16, SEQ ID NO: 17, SEQ ID NO: 18, SEQ ID NO: 19, SEQ ID NO: 20, and SEQ ID NO: 21 or that hybridize under conditions of high stringency to the complement of SEQ ID NO: 16, SEQ ID NO: 17, SEQ ID NO: 18, SEQ ID NO: 19, SEQ ID NO: 20, and SEQ ID NO: 21. Furthermore, the regulatory region, may comprise any combination of isolated polynucleotides with at least 80% sequence homology to SEQ ID NO: 16, SEQ ID NO: 17, SEQ ID NO: 18, SEQ ID NO: 19, SEQ ID NO: 20, and SEQ ID NO: 21 or the complement of SEQ ID NO: 16, SEQ ID NO: 17, SEQ ID NO: 18, SEQ ID NO: 19, SEQ ID NO: 20, and SEQ ID NO: 21. Accordingly, for example, in one embodiment of the present invention, the regulatory region comprises SEQ ID NO: 16, SEQ ID NO: 17, SEQ ID NO: 18, from 1 to about 3 copies of SEQ ID NO: 20, and SEQ ID NO: 21. In yet another embodiment, the regulatory region comprises SEQ ID NO: 16, SEQ ID NO: 17, SEQ ID NO: 20, and SEQ ID NO: 21.

The polynucleotides comprising regulatory regions of the present invention may be isolated by any method generally known in the art for isolating non-coding regions of nucleic acid sequence. One such method comprises employing hybridization of a probe to a genomic library to detect shared nucleotide sequence and is detailed in, for example, Sambrook et al., *Molecular Cloning, A Laboratory Manual*, 2nd ed., Cold Spring Harbor Laboratory Press, (1989) and Ausubel et al., *Short Protocols in Molecular Biology*, 3rd ed., John Wiley & Sons (1995).

Also included are vectors comprising the isolated polynucleotide regulatory sequences of the invention or the complement thereof, as set-forth in detail above. Any vector suitable for propagation in yeast may be employed such as, for example, pIB1 (Sears et al., (1998) Yeast 14: 783–90), pPICZ (commercially available through Invitrogen, Carlsbad, Calif.) vector series, and pPIC9K (commercially available through Invitrogen, Carlsbad, Calif.). The vector may also be either a cloning vector or an expression vector. A cloning vector is a self-replicating DNA molecule that serves to maintain a DNA segment into a host cell. The most common type of cloning vectors are bacterial plasmids. An expression vector is a cloning vector designed so that a sequence inserted at a particular site will be transcribed into mRNA and in addition may be translated into a protein. Both cloning and expression vectors usually contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences. Various bacterial and yeast origins of replication are well known to those skilled in the art and include, but are not limited to, the pBR322 plasmid origin, and the 2 μplasmid origin. Ausubel et al., ed., *Short Protocols in Molecular Biology*, 3rd ed., Wiley & Sons, 1995.

The isolated polynucleotide comprising regulatory sequences of the present invention may be inserted into the vector by a variety of methods. In yet a further embodiment, the isolated polynucleotide comprising regulatory regions operably linked to a heterologous coding region may be inserted into the vector. In the most common method, the sequence is inserted into an appropriate restriction endonuclease site(s) using procedures commonly known to those skilled in the art and detailed in, for example, Sambrook et al., *Molecular Cloning, A Laboratory Manual*, 2nd ed., Cold Spring Harbor Laboratory Press, (1989) and Ausubel et al., *Short Protocols in Molecular Biology*, 3rd ed., John Wiley & Sons (1995).

Expression and cloning vectors can and usually do contain a selection gene or selection marker. Typically, this gene encodes a protein necessary for the survival or growth of the host cell transformed with the vector. Examples of suitable selection markers include, HIS4, ARG4, ble, and kan (Cregg et al., (2000) Mol. Biotech. 16: 23–52). The selection marker can have its own promoter so that expression of the marker occurs independent of the polynucleotide construct. The marker promoter can be either a constitutive or an inducible promoter.

In a further embodiment, the vector of the present invention also typically will include a sequence that is homologous with the host's sequence at a particular gene loci, for example a portion of the His4 gene or AOX gene (both yeast genes), to enable the vector to insert into the host's chromosome by homologous recombination. Preferably, the homologous sequence employed in the invention will be at least approximately 200 nucleotides in length and have homology to yeast genomic DNA. Applicants have found that such integration is desirable, particularly when the host is *P. pastoris*, because vectors that are not integrated tend to be unstable.

More particularly, in another embodiment is provided a recombinant polynucleotide comprising any of the above described regulatory regions of the invention operably linked to a heterologous coding region. Such recombinant polynucleotides are commonly employed in cloning or expression vectors (as detailed above), although other uses are possible. The heterologous coding region may encode any protein of interest suitable for expression in the host cell such as enzymes, hormones, regulatory proteins, structural proteins, or antigens (for use in inducing an immune response).

The isolated polynucleotides of the present invention may be part of an expression cassette that minimally comprises, operably linked in 5' to 3' direction, a polynucleotide comprising a regulatory region of the present invention, a heterologous coding region and a transcriptional termination signal sequence functional in a host cell. The expression cassette may comprise any of the isolated polynucleotide regulatory regions of the invention, as previously discussed. Additionally, the heterologous coding region may encode any protein of interest suitable for expression in the host cell such as enzymes, hormones, regulatory proteins, structural proteins, or antigens (for use in inducing an immune response).

In a further embodiment, the expression cassette can also comprise an operably linked targeting sequence, transit or secretion peptide coding region capable of directing transport of the protein produced to the desired location. The expression cassette may also further comprise a nucleotide sequence encoding a selectable marker and/or a purification moiety. Various methods have been devised for the addition of such affinity purification moieties to proteins. Representative examples can be found in U.S. Pat. Nos. 4,703,004, 4,782,137, 4,845,341, 5,935,824, and 5,594,115. Any method known in the art for the addition of nucleotide sequences encoding purification moieties can be used for example those contained in Innis et al., *PCR Protocols*, Academic Press (1990) and Sambrook et al., *Molecular Cloning*, 2nd ed., Cold Spring Harbor Laboratory Press (1989). In yet another embodiment, the expression cassette can comprise a sequence that is homologous with the host's sequence at a particular gene loci to enable the cassette to insert into the host's chromosome by homologous recombination.

Encompassed within the present invention are host cells transformed with any of the constructs described herein comprising the polynucleotide regulatory sequences of the invention. The host cell is preferably a yeast cell. Yeast are preferred hosts because their usage provides a means to regulate gene expression when the regulatory sequences of the invention are employed. As stated above, the regulatory regions of the invention are repressible in response to repressing carbon sources (e.g. glucose, ethanol, fructose, galactose, sucrose and glycerol) and inducible in response to non-repressing carbon sources (e.g. sorbital, mannitol, threhalose, and alanine) when subjecting the transformed yeast to carbon starvation. Accordingly, gene expression can be strictly regulated based upon the medium selected to grow the cells.

Even more preferably, however, the host will be a methylotrophic yeast cell. Still more preferably, the methylotrophic yeast cell is selected from the group of genera consisting of Hansenula, Candida, Torulopsis and Pichia. Even more preferably, the yeast cell is from $P.$ $pastoris$. The use of methylotrophic yeast provides an additional means to control gene expression when employing the regulatory regions of the invention. Methylotrophic yeast, as opposed to yeast in general, are capable of growth on methanol as their sole carbon and energy source. In addition, as delineated above, methanol is a strong inducer of the regulatory sequences of the invention. For example, in methanol grown $P.$ $pastoris$ cells, AOX rapidly accumulates up to 30% of the total soluble protein. Thus, the use of methylotrophic yeast as host cells in the present invention provides a mechanism to both reliably control gene expression and at the same time, achieve a high rate of expression. Introduction of the construct into the host cell can be accomplished by any method known in the art.

The present invention also includes methods for the production of proteins from the above described host cells transformed with any of the constructs characterized herein containing the polynucleotide regulatory regions of the present invention operably linked to a gene encoding the desired protein. Proteins can be expressed in any suitable host cells, but are preferably expressed in yeast host cells for the reasons previously identified. Host cells are genetically transformed to produce the protein of interest by introduction of an expression vector containing the nucleic acid sequence of interest. The characteristics of suitable cloning vectors and the methods for their introduction into host cells have been previously discussed. Methods for such protein production are known to those skilled in the art. (Davis et al., $Basic$ $Methods$ $in$ $Molecular$ $Biology$, Elsevier Science Publishing (1986); Ausubel et al., $Short$ $Protocols$ $in$ $Molecular$ $Biology$, $2^{nd}$ Ed., John Wiley & Sons (1992)).

Host cells are grown under appropriate conditions to a suitable cell density to optimize expression of the protein. If the protein accumulates in the host cell, the cells are harvested by, for example, centrifugation or filtration. The cells are then disrupted by physical or chemical means to release the protein into the cell extract from which the protein can be purified. If the host cells secrete the protein into the medium, the cells and medium are separated and the medium retained for purification of the protein.

Larger quantities of protein can be obtained from cells carrying amplified copies of the sequence of interest. In this method, the sequence is contained in a vector that carries a selectable marker and transfected into the host cell or the selectable marker is co-transfected into the host cell along with the sequence of interest. Lines of host cells are then selected in which the number of copies of the sequence have been amplified. A number of suitable selectable markers will be readily apparent to those skilled in the art. For example, the sh ble gene is widely used as a maker for co-amplification. The sh ble gene product confers resistance to the drug Zeocin in both $E.$ $coli$ and yeast.

Proteins recovered can be purified by a variety of commonly used methods, including, but not limited to, ammonium sulfate precipitation, immuno precipitation, ethanol or acetone precipitation, acid extraction, ion exchange chromatography, size exclusion chromatography, affinity chromatography, high performance liquid chromatography, electrophoresis, and ultra filtration. If required, protein refolding systems can be used to complete the configuration of the protein.

The polynucleotide encoding the regulatory sequences of the invention, as described in detail above, may be employed to increase the expression of genes of interest in a variety of host cells. However, applicants discovery, in addition to increased gene expression, may also be employed for a number of other functions. For example, the regulatory sequences of the invention may be employed in a research setting to further characterize promoter function and to study peroxisome biogenesis.

The detailed description set-forth above is provided to aid those skilled in the art in practicing the present invention. Even so, this detailed description should not be construed to unduly limit the present invention as modifications and variation in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

Without further elaboration, it is believed that one skilled in the art can, using the preceding description, utilize the present invention to its fullest extent. The following preferred specific embodiments are, therefore, to be construed as merely illustrative, and not imitative of the remainder of the disclosure in any way whatsoever.

EXAMPLE

Materials and Methods

Strains and Plasmids.

Plasmid pSAOH5 (Tschopp et al., (1987) Nucleic Acids Res. 15: 3859–76) and $P.$ $pastoris$ GS115 (Tschopp et al., (1987) Nucleic Acids Res. 15: 3859–76) (his4) strain were the generous gift of J. M. Cregg, Keck Graduate Institute, Claremont, Calif. pIB1 promoter less expression vector was provided by B. S. Glick (University of Chicago, Chicago, Ill.). $E.$ $coli$ strains JM109 (endA1, recA1, gyrA96, thi, hsdR17($r_k^-$, $m_k^+$), relA1, supE44, l⁻, D(lac⁻proAB), [F′, traD36, proA⁺B⁺, lacI$^q$ZDM15] and ES1301 mutS (LacZ53, mutS201::Tn5, thyA36, rha⁻5, metB1, deoC,IN (rrnD-rrnE), pALTER®-1 plasmid were purchased as a components of Altered Sites® II in vitro Mutagenesis System (Promega, Madison, Wis.).

Media, growth conditions and enzymatic analysis. Yeasts were grown in minimal glycerol media (MGY: 1.34% yeast nitrogen base without amino acids, 1% glycerol, $4\times10^{-5}$% biotin) and transformed cells were selected on Minimal Dextrose (MD) plates (1.34% yeast nitrogen base without amino acids (YNB), 2% glucose, $4\times10^{-5}$% biotin and 1.5% agar). If required 0.0004% histidine was added to the media.

The cells were grown on Minimal Methanol (MM, 1.34% YNB, $4\times10^{-5}$% biotin, 0.5% methanol) and Minimal Methanol-Ethanol (MME, 1.34% YNB, $4\times10^{-5}$% biotin, 0.5% methanol and 0.5% ethanol) until the optical density (600 nm) reached to 1.5–2.0 at 30° C. β-Gal activity was assayed using ONPG (o-Nitrophyenyl B-D-glactopyranoside) as reported by Miller, J. H. Assay of β-galactosidase. in Miller, J. H. (ed), *Experiments in Molecular Genetic*, Cold Spring Harbor Laboratory, pp. 352–355 (1972) incorporating the modification proposed by Guarente and Ptashne, Fusion of *Escherichia coli* lacZ to the cytochrome c gene of *Saccharomyces cerevisiae. Proc. Natl. Acad. Sci. USA* 78, 2199–203 (1981). The cells were permeabilized with chloroform and sodium dodecyl sulfate (SDS) and the results were reported in Miller Units.

General DNA Techniques.

Restriction enzymes and primers were from New England Biolabs Inc. (Beverly, Mass.), Site Directed Mutagenesis (SDM) was performed with the Altered Sites® II in vitro Mutagenesis System from Promega (Madison, Wis.) according to the manufacturer's recommendations. Primers were purchased from Sigma/Genosys (The Woodlands, Tex.). Protocols for the system were followed as described in the technical manual. All other DNA manipulations were as previously described (Sambrook, et al., (1989) Molecular Cloning: A Laboratory Manual). A 1.5 Kb HIS4 fragment from pAL2 was used for Southern analysis to select single copy transformants.

Plasmid Constructions.

The plasmid pSAOH5 was first used as the parental plasmid to characterize the regulation of LacZ gene under the control of the AOX1 promoter of *P. pastoris*. pAL2, an integrating plasmid, was constructed because of instability of the plasmid pSAOH5 in *P. pastoris*. The 3.6 kb Eco RI-Nru I fragment of pSAOH5 was inserted in the Eco RI-Sma I region of the pIB1, promoter less Pichia expression vector, and pAL2 parental plasmid was obtained. The Eco RI/Nru I fragment of pSAOH5 contained the 5' untranslated region and first 15 amino acids of AOX1 fused to the lacZ gene at codon nine. The mutagenesis plasmid, pMMI101, was constructed by inserting a 1120 base pair Eco RI-Bam HI fragment of pSAOH5 into pALTER-1 (FIG. 1).

The plasmids containing 5' deletion derivatives of the AOX1 promoter were constructed using the Altered Sites® II in vitro Mutagenesis System to insert Eco RI sites at various positions along the promoter element. The primers used to obtain 5' deletion derivatives of the AOX1 promoter are as follows;

```
AOXRI132
5'-ACGCAGGAATTCCTCCACTC-3'     (SEQ ID NO: 22)

AoxRI285
5'-GGCGAGGAATTCATGTTTGT-3'     (SEQ ID NO: 23)

AoxRI424
5'-GTCTTGGAATTCCTAATATGAC-3'   (SEQ ID NO: 24)

AoxRI551
5'-GGTATTGAATTCACGAATGCTC-3'   (SEQ ID NO: 25)

AOXRI699
5'-CTTCCAAGAATTCTGGTGGG-3'     (SEQ ID NO: 26)
```

The mutant plasmids (pMMI132-pMMI669) were digested with Eco RI/Sma I, and the fragments were exchanged with the native AOX1 promoter in pAL2.

The construction of PALD series which remove internal AOX1 promoter sequences was as follows: PMMI series of plasmids, pMMI132, pMMI285, pMMI424 and pMMI551 which carry the mutant Eco RI sites and deletes the 5' upstream AOX1 promoter fragments, A (SEQ ID NO: 16), AB (SEQ ID NO: 16 and SEQ ID NO: 17, respectively), ABC (SEQ ID NO: 16, SEQ ID NO: 17, and SEQ ID NO: 18, respectively) ABCD (SEQ ID NO: 16, SEQ ID NO: 17, SEQ ID NO: 18, and SEQ ID NO: 19, respectively), respectively. These fragments were inserted into the expression plasmids carrying the sequential deletion derivatives of the AOX1 promoter, pAL285, pAL424, pAL551, pAL669, and the plasmids were named pALD1, pALD2, pALD3 and pALD4, respectively. Consequently each PALD plasmid lacks B (SEQ ID NO: 17), C (SEQ ID NO: 18), D (SEQ ID NO: 19) and E (SEQ ID NO: 20) promoter fragments respectively.

In order to purify the regions of the fragments (B (SEQ ID NO: 17), C (SEQ ID NO: 18), D (SEQ ID NO: 19) and E (SEQ ID NO: 20)) for band shift assay, a second round of site directed mutagenesis was done. The pMMI132, pMMI285, pMMI424, pMMI551 ssDNAs and AOXRI285, AOXRi424, AOXRI551 and AOXR1669 primers were used for SDM (site directed mutagenesis) reactions to drop B (SEQ ID NO: 17), C (SEQ ID NO: 18), D (SEQ ID NO: 19) and E (SEQ ID NO: 20) fragment, respectively. For example, to purify fragment B (SEQ ID NO: 17), pMMI132 single stranded DNA and primer AOX1285 were used to insert a third EcoRI site into the AOX1 promoter. After sited directed mutagenesis, each of fragments A (SEQ ID NO: 16), B (SEQ ID NO: 17), C (SEQ ID NO: 18), D (SEQ ID NO: 19), E (SEQ ID NO: 20) and F (SEQ ID NO: 21) was gel purified with a Gene Clean II Kit (Bio101, Inc. Vista, Calif.).

Prior to transformation, the deletion and chimen c plasmids were digested with Stu I, which cuts the vectors once within the HIS4 sequences to direct the integration event in the his4 locus of the host GS115 strain. Transformants were selected on MD media which lacks histidine. A single copy of the plasmids of transformed strains of transformed strains was determined by Southern blot assay. At least three independent single-copy transformants were chosen, induced in MM media, and β-Gal activity was monitored in the strains. One representative strain was used for further studies. At least three independent induction experiments in MM and MME media were done to estimate the β-gal activity.

DNA Probes for Gel Shift Assays.

Second round SDM (site directed mutagenesis) was done to purify plasmids pMMI132, pMMI285, pMMI424, pMMI551 to release fragments B (SEQ ID NO: 17), C (SEQ ID NO: 18), D (SEQ ID NO: 19) and E (SEQ ID NO: 20), respectively. The Eco RI fragment of pMMI132 and the Eco RI/Sma I fragment of pMMI669 were used as fragments A (SEQ ID NO: 16) and F (SEQ ID NO: 21), respectively. Each fragment was purified from agarose gel and end labeled with DNA polymerase using infrared labeled DATP (Li-Cor Inc, Lincoln, Nebr.)

Preparation of Yeast Cell Extracts.

Yeasts were grown in 25 ml of MM or MME media at 30° C. to 1.5 OD (600 nm). The cells were centrifuged at 2,000×g at room temperature, washed twice with 1M sorbitol and suspended in 500 ml of Buffer C [20 mM HEPES pH 8.0, 0.2 mM EDTA, 0.5 mM dithiotretiol (DTT), 0.5 mM PMSF (phenylmethylsulfonyl fluoride), 0.42 M NaCl, 1.5 mM $MgCl_2$ and 25% glycerol]. The cells were broken with glass beads (0.45–0.5 mmin diameter) in a bead beater (Biospec Products) (7×30 sec). After centrifugation at 19,000×g for 15 minutes at 4° C., the supernatant was used for gel retardation assays. Total protein from cell extracts was estimated by the BCA assay (Pierce) using BSA as a standard protein.

Gel retardation assay. The binding reaction mixtures contained 20 mM Tris-HCl (pH 7.5), 100 mM NaCl, 1 mM DTT, 2 mg of poly (dI-dC)•poly (dI-dC) (deoxyinosine-deoxycytosine), 0.05% Nonidet-40, 10% glycerol and end-labeled DNA in a volume of 20 ml. The binding reaction mixtures included 6 mg of protein extract. After 20 min of incubation at room temperature, mixtures were loaded on to a 6% non-denaturing pre-casted polyacrylamide gel (Novex, Carlsbad, Calif.). Electrophoresis was carried out at 10 v/cm of gel for 90 min in TBE (45 mM Tris/borate, 1 mM EDTA). The gels were dried and scanned with a prototype Y-axis scanner using Base ImagIR v. 4.0 software (Li-Cor, Lincoln, Nebr.).

Results

Regulation of Deletion Derivatives of AOX1 Promoter.

The plasmids carrying sequential deletions (pAL series) and dropout mutations (pDAL series) were integrated into the his4 locus of chromosome of P. pastoris GS115 strain and single-copy transformants were screened by Southern blot analysis (results not shown). At least three single-copy transformants were screened by β-gal expression in MM medium, and one representative strain was used for further induction experiments. Each transformant was cultured in MGY (minimal glycerol media) media overnight. The culture was used to inoculate MM and MME media, with cells were grown to an optical density of 1.5–2.0 (600 nm) prior to harvesting. The activity of the AOX1-lacZ fusion was measured and reported as percent of activity of methanol-grown cells containing pAL2.

Each of the deletion derivatives of the AOX1 promoter decreased β-Gal activity in MM media compared to the native promoter (FIG. 2). Loss of fragment D (SEQ ID NO: 19)(−518/−390) (pAL551) resulted in about a two-fold increase of β-gal activity, relative to pAL424, while loss of fragment E (SEQ ID NO: 20) (−390/−239) had the most severe effect on the expression.

The sequential deletions do not always reflect the relative promoter activity since the cumulative effect of cis-acting sequences is neglected. Therefore, a series of AOX1 promoter derivatives were constructed with internal deletions (pALDs) to determine the exclusive effect of each fragment. Only loss of sequences B (SEQ ID NO: 17) and E (SEQ ID NO: 20) had a significant effect on lacZ expression, suggesting that positive elements are located within these deletion intervals. The most significant effect on β-gal activity was observed by deletion of the fragment E (SEQ ID NO: 20)(−390/−239) where the AOX1 promoter lost 84% of activity.

Although the deletion derivatives of the AOX1 promoter had a significant effect on the promoter activity of methanol grown cells, the deletion and dropout plasmids did not impair ethanol induced repression of the AOX1 promoter (FIG. 2).

Gel Retardation Assays.

The GS115 (pAL2) strain was used to obtain total protein extracts growing in repressed (MME) or induced (MM) conditions. The fragments A, B, C, D, E and F (SEQ ID NO: 16, SEQ ID NO: 17, SEQ ID NO: 18, SEQ ID NO: 19, SEQ ID NO: 20, and SEQ ID NO: 21, respectively) were tested in gel-shift assays. The fragment A (SEQ ID NO: 16) resulted in formation of specific DNA-protein complex when the cells were grown under induced condition (methanol) (FIG. 3, lane 2). However, the ethanol grown cell-protein extracts did not reveal any DNA-protein complexes (FIG. 3, lane 6). Specificity was tested by adding unlabeled competitor and unlabeled nonspecific DNA (Lanes 3 and 5). Two mg poly dI.dC poly dI.dC and 500-bp *Listeria moncytogenes* gene product were used as nonspecific DNAs. The addition of competitor (unlabeled A fragment) resulted in loss of the signal (lane 3). Furthermore, addition of the unlabeled fragment C (SEQ ID NO: 18)(lane 4) did not compete with fragment A (SEQ ID NO: 16) implying that DNA binding for the fragment C (SEQ ID NO: 18) is specific and the protein binding to fragment A (SEQ ID NO: 16) does not form a complex with fragment C (SEQ ID NO: 18).

The gel shift assay using fragment C (SEQ ID NO: 18) and total protein extracted from yeast cells under induced and un-induced conditions revealed the formation of specific DNA-protein complexes. In this case the fragment A (SEQ ID NO: 16) and nonspecific DNA (*L. monocytogenes* DNA) did not compete for the protein (FIG. 4, lanes 4,8 and lanes 5, 9, respectively).

Extract from ethanol/methanol grown cells forms a complex with fragment C (SEQ ID NO: 18), but the intensity of the signal was weaker than that observed with methanol grown cells using the same amount of total cell extract (6 mg total protein).

Figure 5:
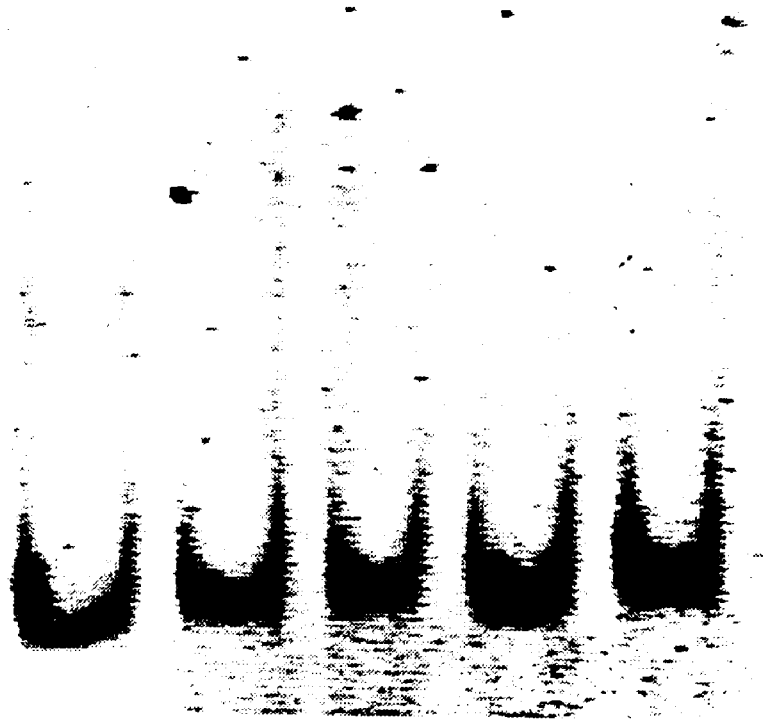
FIG. 5 depicts results of the gel shift assay for fragment F (SEQ ID NO: 21). Lane 1, no protein added; lane 2, six mg protein from MM grown cells; lane 3, twelve mg protein from MM grown cells; lane 4, six mg protein from MME grown cells; lane 5, twelve mg protein from MME grown cells.

The gel shift assays using the fragments B (SEQ ID NO: 17), D (SEQ ID NO: 19), E (SEQ ID NO: 20), and F (SEQ ID NO: 21) did not reveal any DNA-protein complexes, although different gel-shift experiment conditions were tested (results not shown). The gel shift results of the fragment F (SEQ ID NO: 21) is shown in FIG. 5. Additionally, FIG. 6 depicts consensus sequences of methanol regulated promoters of methylotrophic yeast.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. An isolated polynucleotide consisting of the nucleotide sequence as set forth in SEQ ID NO: 20.
2. An isolated polynucleotide consisting of the nucleotide sequence as set forth in SEQ ID NO: 27.
3. An isolated polynucleotide consisting of the nucleotide sequence as set forth in SEQ ID NO: 28.
4. An isolated polynucleotide consisting of the nucleotide sequence as set forth in SEQ ID NO: 29.
5. A recombinant vector comprising a 5' regulatory sequence operably linked to a heterologous coding region wherein the 5' regulatory sequence consists of the isolated polynucleotide of any of claims 1–4.
6. An expression cassette comprising operably linked in 5' to 3' order a 5' regulatory sequence, a heterologous coding region, and a termination sequence wherein said 5' regulatory sequence consists of the isolated polynucleotide of any of claims 1–4.
7. A host cell comprising the vector of claim 5.
8. The host cell of claim 7 wherein said host cell is a yeast cell.
9. The host cell of claim 8 wherein said yeast cell is a methylotrophic yeast cell.
10. The host cell of claim 9 wherein said methylotrophic yeast cell is selected from the group of genera consisting or Hansenula, Cadida, Torulopsis, and Pichia.
11. The host cell of claim 10 wherein said methylotrophic yeast cell is a cell of Pichia pastoris.
12. A host cell comprising the expression cassette of claim 6.
13. The host cell of claim 12 wherein said host cell is a yeast cell.
14. The host cell of claim 13 wherein said yeast cell is a methylotrophic yeast cell.
15. The host cell of claim 14 wherein said methylotrophic yeast cell is selected from the group of genera consisting of Hansenula, Candida, Torulopsis and Pichia.
16. The host cell of claim 15 wherein said methylotrophic yeast cell is a cell of Pichia pastoris.
17. The host cell of claim 7 wherein said host cell expresses a protein encoded by said vector.
18. The host cell of claim 12 wherein said host cell expresses a protein encoded by said expression cassette.
19. A method for the production of a protein comprising growing the host cell of claim 17 under conditions where said host cell expresses the protein encoded by said vector and isolating the expressed protein.
20. A method for the production of a protein comprising growing the host cell of claim 18 under conditions where said host cell expresses the protein encoded by said vector and isolating the expressed protein.

* * * * *

SEQUENCE LISTING

<160> NUMBER OF SEQ ID NOS: 29

<210> SEQ ID NO 1
<211> LENGTH: 1052
<212> TYPE: DNA
<213> ORGANISM: Pichia pastoris

<400> SEQUENCE: 1

```
aattcccgct tgatgcctg aaatcccagc gcctacaatg atgacatttg gatttggttg      60
actcatgttg gtattgtgaa atagacgcag atcgggaaca ctgaaaaata acagttatta    120
ttcgagatct aacatccaaa gacgaaaggt tgaatgaaac cttttttgcca tccgacatcc   180
acaggtccat tctcacacat aagtgccaaa cgcaacagga ggggatacac tagcagcaga    240
ccgttgcaaa cgcaggactc atcctcttct ctaacaccat tttgcatgaa acagccagt     300
tatgggcttg atggagctcg ctcattccaa ttccttctat taggctacta acaccatgac    360
tttattagcc tgtctatcct ggccccctg gcgaggtcat gttttgttat ttccgaatgc     420
aacaagctcc gcattacacc cgaacatcac tccagatgag ggctttctga gtgtggggtc    480
aaatagtttc atgttcccaa atggcccaaa actgacagtt taaacgctgt cttggaacct   540
aatatgacaa agcgtgatc tcatccaaga tgaactaagt ttggttcgtt gaaatcctaa     600
cggccagttg gtcaaaaaga aacttccaaa agtcgccata ccgtttgtct tgtttggtat   660
tgattgacga atgctcaaaa ataatctcat taatgcttag cgcagtctct ctatcgcttc    720
tgaacccggt ggcacctgtg ccgaaacgca aatggggaaa caacccgctt tttggatgat   780
tatgcattgt cctccacatt gtatgcttcc aagattctgg tgggaatact gctgatagcc    840
taacgttcat gatcaaaatt taactgttct aaccctact tggacaggca atatataaac    900
agaaggaagc tgccctgtct taaaccttt ttttttatcat cattattagc ttactttcat    960
aattgcgact ggttccaatt gacaagcttt tgattttaac gactttaac gacaacttga   1020
gaagatcaaa aaacaactaa ttattcgaaa cg                                 1052
```

<210> SEQ ID NO 2
<211> LENGTH: 1757
<212> TYPE: DNA
<213> ORGANISM: Pichia pastoris

<400> SEQUENCE: 2

```
ggatctcaaa aacctaagta cttcatttga atataactct gcacctaaaa tttacaccta    60
actctctatc taggctctag atttgataga ttctatagcc tttggttgt tatagtgttc    120
accaactgga tgtcctaacg aaatggttct gtggtctagt tggttatggc atatgcttaa   180
cacgcaaacg tccccagttc gatcctgggc agaatcatta ttttttgacc gaattctttt   240
tttcagacca tatgaccggt ccatcttcta cggggggatt atctatgctt tgacctctat    300
cttgattctt ttatgattca atcacttttt acgttattta ttacttactg gttatttact    360
tagcgccttt tctgaaaaac atttactaaa aatcatacat cggcactcta aacacgacag   420
attgtgatca agaagcagag acaatccacca ctaaggttgc catttgagc cagtaggctc    480
ctaatagagg ttcgatactt attttgataa tacgacatat tgtcttacct ctgaatgtgt    540
caatactctc tcgttcttcg tctcgtcagc taaaaatata acacttcgag taagatacgc   600
ccaattgaag gctacgagat accagactat cactagtaga actttgacat ctgctaaagc    660
agatcaaata tccatttatc cagaatcaat taccttcctt tagcttgtcg aaggcatgaa   720
```

```
aaagctacat gaaaatcccc atccttgaag ttttgtcagc ttaaaggact ccatttccta    780
aaatttcaag cagtcctctc aactaaattt ttttccattc ctctgcaccc agccctcttc    840
atcaaccgtc cagcttctca aaagtccaat gtaagtagcc tgcaaattca ggttacaacc    900
cctcaatttt ccatccaagg gcgatcctta caaagttaat atcgaacagc agagactaag    960
cgagtcatca tcaccaccca acgatggtga aaaactttaa gcatagattg atggagggtg   1020
tatggcactt ggcggctgca ttagagtttg aaactatggg gtaatacatc acatccggaa   1080
ctgatccgac tccgagatca tatgcaaagc acgtgatgta ccccgtaaac tgctcggatt   1140
atcgttgcaa ttcatcgtct aaacagtac aagaaacttt attcatgggt cattggactc    1200
tgatgagggg cacatttccc caatgatttt ttgggaaaga aagccgtaag aggacagtta   1260
agcgaaagag acaagacaac gaacagcaaa agtgacagct gtcagctacc tagtggacag   1320
ttgggagttt ccaattggtt ggttttgaat ttttacccat gttgagttgt ccttgcttct   1380
ccttgcaaac aatgcaagtt gataagacat caccttccaa gataggctat ttttgtcgca   1440 taaattttg tctcggagtg aaaacccctt ttatgtgaac agattacaga agcgtcctac    1500
ccttcaccgg ttgagatggg gagaaaatta agcgatgagg agacgattat tggtataaaa   1560
gaagcaacca aaatcccttta ttgtccttttt ctgatcagca tcaaagaata ttgtcttaaa  1620
acgggctttt aactacattg ttcttacaca ttgcaaacct cttccttcta tttcggatca   1680
actgtattga ctacattgat ctttttttaac gaagtttacg acttactaaa tccccacaaa  1740
caaatcaact gagaaaa                                                    1757

<210> SEQ ID NO 3
<211> LENGTH: 1095
<212> TYPE: DNA
<213> ORGANISM: Pichia pastoris

<400> SEQUENCE: 3
ctgcagcttt gataccctgaa attcctgagc ctataataat gacttttgca ctctgttggc    60
tcatgacgat tttgttgaaa tgaatcttca caagaagagc tcaattgagt agagataatt   120
agtaagtgag atccaacacc caggaacgag atggattcag gagaaattgt tctgccatcc   180
gacatcgaca agttagacac aatagtgcca aatgcagagg ggacgtttcc tcaaggcaag   240
aactccactt tattcctcct caaacacccg ccttcgccgt taaaaaccag cccagttact   300
aaacatggtt tggactctct ctaatccact ttgttaggct actagtagca ttattttctt   360
agcctgtcta tatggttcct tgcgagtttt taattttatt tctatttccg aatgtaactt   420
actccgcatt ccatcccaac accagaaagt tgagggtttt tgtgagtgtg gggtcggtaa   480
cagtttcatg ttcccccaat ggcctaaaat tgacacttta gacgccctgt tcaaactcaa   540
attgacaaaa gcgtgatctc atcagagatg aactaggttt ggttcgatca aaagctaacg   600
gccagttggt caaaaagaaa cttccaatgt cggcataccg tttgtttcgt ttgacccgac   660
aattgatgtt gaagaattcc ctcttacact agcgcagcc tttattttgc ttggggtctc    720
gctgcgcttg ggtctcggtg tgcttgtgac cggaaacgca aatggggaaa cacccgcttt   780
ttggatgatt atgcattgtt ctccacattg tatgcttcca gtttctggt gggaatactg     840 atagcctaac gttcatgatc aaaactaatg tcttccctac ttgaacagca atatataaac    900
agaagaagat ttcctttcta aggtcttttt ttttatcatc attatcagct tactttcata    960
attgtgactg gttccaattg acaagctttt gattctaacg actttaacga caacctaaag   1020
```
aacaaaaaca actaattatt cgaaacaatg gctattcccg aagaatttga tattatcgtc     1080
tgtggtggtg gatcc                                                      1095

<210> SEQ ID NO 4
<211> LENGTH: 21
<212> TYPE: DNA
<213> ORGANISM: Yeast
<220> FEATURE:
<221> NAME/KEY: misc_feature
<222> LOCATION: (4)..(4)
<223> OTHER INFORMATION: n=unknown
<220> FEATURE:
<221> NAME/KEY: misc_feature
<222> LOCATION: (5)..(5)
<223> OTHER INFORMATION: n=unknown
<220> FEATURE:
<221> NAME/KEY: misc_feature
<222> LOCATION: (6)..(6)
<223> OTHER INFORMATION: n=unknown
<220> FEATURE:
<221> NAME/KEY: misc_feature
<222> LOCATION: (16)..(16)
<223> OTHER INFORMATION: n=unknown
<220> FEATURE:
<221> NAME/KEY: misc_feature
<222> LOCATION: (17)..(17)
<223> OTHER INFORMATION: n=unknown
<220> FEATURE:
<221> NAME/KEY: misc_feature
<222> LOCATION: (15)..(15)
<223> OTHER INFORMATION: n=unknown

<400> SEQUENCE: 4
ttgnnngctt ccaannntgg t                                                21

<210> SEQ ID NO 5
<211> LENGTH: 10
<212> TYPE: DNA
<213> ORGANISM: Yeast
<220> FEATURE:
<221> NAME/KEY: misc_feature
<222> LOCATION: (3)..(3)
<223> OTHER INFORMATION: n=unknown

<400> SEQUENCE: 5 ccncttttg                                                              10

<210> SEQ ID NO 6
<211> LENGTH: 16
<212> TYPE: DNA
<213> ORGANISM: Yeast

<400> SEQUENCE: 6
gctcattcca attcct                                                      16

<210> SEQ ID NO 7
<211> LENGTH: 16
<212> TYPE: DNA
<213> ORGANISM: methylotrophic yeast

<400> SEQUENCE: 7
ctgtcttgga acctaa                                                      16

<210> SEQ ID NO 8
<211> LENGTH: 16
<212> TYPE: DNA
<213> ORGANISM: methylotrophic yeast

<400> SEQUENCE: 8

```
gaaacttcca aaagtc                                                    16

<210> SEQ ID NO 9
<211> LENGTH: 16
<212> TYPE: DNA
<213> ORGANISM: methylotrophic yeast

<400> SEQUENCE: 9
tatgcttcca agattc                                                    16

<210> SEQ ID NO 10
<211> LENGTH: 16
<212> TYPE: DNA
<213> ORGANISM: methylotrophic yeast

<400> SEQUENCE: 10
actggttcca attgac                                                    16

<210> SEQ ID NO 11
<211> LENGTH: 15
<212> TYPE: DNA
<213> ORGANISM: methylotrophic yeast

<400> SEQUENCE: 11
cctgtctatc ctggc                                                     15

<210> SEQ ID NO 12
<211> LENGTH: 15
<212> TYPE: DNA
<213> ORGANISM: methylotrophic yeast

<400> SEQUENCE: 12
tctctctatc gcttc                                                     15

<210> SEQ ID NO 13
<211> LENGTH: 15
<212> TYPE: DNA
<213> ORGANISM: methylotrophic yeast

<400> SEQUENCE: 13
ctgctgatag cctaa                                                     15

<210> SEQ ID NO 14
<211> LENGTH: 15
<212> TYPE: DNA
<213> ORGANISM: methylotrophic yeast

<400> SEQUENCE: 14
gagttcgagg tcgtg                                                     15

<210> SEQ ID NO 15
<211> LENGTH: 15
<212> TYPE: DNA
<213> ORGANISM: methylotrophic yeast

<400> SEQUENCE: 15
gagtgtgggg tcaaa                                                     15

<210> SEQ ID NO 16
<211> LENGTH: 256
<212> TYPE: DNA
<213> ORGANISM: Pichia pastoris
```

-continued

```
<400> SEQUENCE: 16
aattcccgct tgatgcctg aaatcccagc gcctacaatg atgacatttg gatttggttg        60
actcatgttg gtattgtgaa atagacgcag atcgggaaca ctgaaaaata acagttatta       120
ttcgagatct aacatccaaa gacgaaaggt tgaatgaaac cttttttgcca tccgacatcc     180 acaggtccat tctcacacat aagtgccaaa cgcaacagga ggggatacac tagcagcaga     240
ccgttgcaaa cgcagg                                                       256

<210> SEQ ID NO 17
<211> LENGTH: 140
<212> TYPE: DNA
<213> ORGANISM: Pichia pastoris

<400> SEQUENCE: 17
actcatcctc ttctctaaca ccattttgca tgaaaacagc cagttatggg cttgatggag       60
ctcgctcatt ccaattcctt ctattaggct actaacacca tgactttatt agcctgtcta     120
tcctggcccc cctggcgagg                                                   140

<210> SEQ ID NO 18
<211> LENGTH: 139
<212> TYPE: DNA
<213> ORGANISM: Pichia pastoris

<400> SEQUENCE: 18
tcatgtttgt ttatttccga atgcaacaag ctccgcatta cacccgaaca tcactccaga       60
tgagggcttt ctgagtgtgg ggtcaaatag tttcatgttc ccaaatggcc caaaactgac      120
agtttaaacg ctgtcttgg                                                    139

<210> SEQ ID NO 19
<211> LENGTH: 127
<212> TYPE: DNA
<213> ORGANISM: Pichia pastoris

<400> SEQUENCE: 19
aacctaatat gacaaaagcg tgatctcatc caagatgaac taagtttggt tcgttgaaat       60
cctaacggcc agttggtcaa aagaaaactt ccaaaagtcg ccataccgtt tgtcttgttt     120
ggtattg                                                                 127

<210> SEQ ID NO 20
<211> LENGTH: 151
<212> TYPE: DNA
<213> ORGANISM: Pichia pastoris

<400> SEQUENCE: 20
attgacgaat gctcaaaaat aatctcatta atgcttagcg cagtctctct atcgcttctg       60
aacccggtgg cacctgtgcc gaaacgcaaa tggggaaaca acccgctttt tggatgatta     120
tgcattgtcc tccacattgt atgcttccaa g                                      151

<210> SEQ ID NO 21
<211> LENGTH: 282
<212> TYPE: DNA
<213> ORGANISM: Pichia pastoris

<400> SEQUENCE: 21
attctggtgg gaatactgct gatagcctaa cgttcatgat caaaatttaa ctgttctaac       60
ccctacttgg acaggcaata tataaacaga aggaagctgc cctgtcttaa accttttttt     120
```

```
ttatcatcat tattagctta cttctcataat tgcgactggt tccaattgac aagcttttga       180
ttttaacgac ttttaacgac aacttgagaa gatcaaaaaa caactaatta ttcgaaacga       240
tggctatccc cgaagagttt gatatcctag ttctaggtgg tg                         282
```

```
<210> SEQ ID NO 22
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Primer

<400> SEQUENCE: 22
acgcaggaat tcctccactc                                                    20

<210> SEQ ID NO 23
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Primer

<400> SEQUENCE: 23
ggcgaggaat tcatgtttgt                                                    20

<210> SEQ ID NO 24
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Primer

<400> SEQUENCE: 24
gtcttggaat tcctaatatg ac                                                 22

<210> SEQ ID NO 25
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Primer

<400> SEQUENCE: 25
ggtattgaat tcacgaatgc tc                                                 22

<210> SEQ ID NO 26
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Primer

<400> SEQUENCE: 26
cttccaagaa ttctggtggg                                                    20

<210> SEQ ID NO 27
```

<211> LENGTH: 912
<212> TYPE: DNA
<213> ORGANISM: Artificial Sequence
<220> FEATURE:
<223> OTHER INFORMATION: Derived from SEQ ID NO:1 by deleting
      nt.257-396.

<400> SEQUENCE: 27

| aattcccgct | ttgatgcctg | aaatcccagc | gcctacaatg | atgacatttg | gatttggttg | 60 |
| actcatgttg | gtattgtgaa | atagacgcag | atcgggaaca | ctgaaaaata | acagttatta | 120 |
| ttcgagatct | aacatccaaa | gacgaaaggt | tgaatgaaac | cttttttgcca | tccgacatcc | 180 |
| acaggtccat | tctcacacat | aagtgccaaa | cgcaacagga | ggggatacac | tagcagcaga | 240 |
| ccgttgcaaa | cgcaggtcat | gtttgtttat | ttccgaatgc | aacaagctcc | gcattacacc | 300 |
| cgaacatcac | tccagatgag | ggctttctga | gtgtggggtc | aaatagtttc | atgttcccaa | 360 |
| atggcccaaa | actgacagtt | taaacgctgt | cttggaacct | aatatgacaa | agcgtgatc | 420 |
| tcatccaaga | tgaactaagt | ttggttcgtt | gaaatcctaa | cggccagttg | gtcaaaaaga | 480 |
| aacttccaaa | agtcgccata | ccgtttgtct | tgtttggtat | tgattgacga | atgctcaaaa | 540 |
| ataatctcat | taatgcttag | cgcagtctct | ctatcgcttc | tgaacccggt | ggcacctgtg | 600 |
| ccgaaacgca | aatggggaaa | caacccgctt | tttggatgat | tatgcattgt | cctccacatt | 660 |
| gtatgcttcc | aagattctgg | tgggaatact | gctgatagcc | taacgttcat | gatcaaaatt | 720 |
| taactgttct | aaccccctact | tggacaggca | atatataaac | agaaggaagc | tgccctgtct | 780 |
| taaaccttt | tttttatcat | cattattagc | ttactttcat | aattgcgact | ggttccaatt | 840 |
| gacaagcttt | tgatttttaac | gacttttaac | gacaacttga | aagatcaaa | aaacaactaa | 900 |
| ttattcgaaa | cg | | | | | 912 |

<210> SEQ ID NO 28
<211> LENGTH: 913
<212> TYPE: DNA
<213> ORGANISM: Artificial Sequence
<220> FEATURE:
<223> OTHER INFORMATION: Derived from SEQ ID NO:1 by deleting
      nt.397-535.

<400> SEQUENCE: 28

| aattcccgct | ttgatgcctg | aaatcccagc | gcctacaatg | atgacatttg | gatttggttg | 60 |
| actcatgttg | gtattgtgaa | atagacgcag | atcgggaaca | ctgaaaaata | acagttatta | 120 |
| ttcgagatct | aacatccaaa | gacgaaaggt | tgaatgaaac | cttttttgcca | tccgacatcc | 180 |
| acaggtccat | tctcacacat | aagtgccaaa | cgcaacagga | ggggatacac | tagcagcaga | 240 |
| ccgttgcaaa | cgcaggactc | atcctcttct | ctaacaccat | tttgcatgaa | acagccagt | 300 |
| tatgggcttg | atggagctcg | ctcattccaa | ttccttctat | taggctacta | acaccatgac | 360 |
| tttattagcc | tgtctatcct | ggccccctg | gcgaggaacc | taatatgaca | aaagcgtgat | 420 |
| ctcatccaag | atgaactaag | tttggttcgt | tgaaatccta | acggccagtt | ggtcaaaaag | 480 |
| aaacttccaa | agtcgccat | accgtttgtc | ttgtttggta | ttgattgacg | aatgctcaaa | 540 |
| aataatctca | ttaatgctta | gcgcagtctc | tctatcgctt | ctgaacccgg | tggcacctgt | 600 |
| gccgaaacgc | aaatggggaa | caacccgct | ttttggatga | ttatgcattg | tcctccacat | 660 |
| tgtatgcttc | caagattctg | gtgggaatac | tgctgatagc | ctaacgttca | tgatcaaaat | 720 |
| ttaactgttc | taaccccctac | ttggacaggc | aatatataaa | cagaaggaag | ctgccctgtc | 780 |
| ttaaaccttt | tttttatca | tcattattag | cttactttca | taattgcgac | tggttccaat | 840 |

```
tgacaagctt ttgattttaa cgacttttaa cgacaacttg agaagatcaa aaaacaacta      900
attattcgaa acg                                                         913

<210> SEQ ID NO 29
<211> LENGTH: 925
<212> TYPE: DNA
<213> ORGANISM: Artificial Sequence
<220> FEATURE:
<223> OTHER INFORMATION: Derived from SEQ ID NO:1 by deleting
      nt.536-662.

<400> SEQUENCE: 29
aattcccgct tgatgcctg aaatcccagc gcctacaatg atgacatttg gatttggttg        60
actcatgttg gtattgtgaa atagacgcag atcgggaaca ctgaaaaata acagttatta      120
ttcgagatct aacatccaaa gacgaaaggt tgaatgaaac cttttttgcca tccgacatcc     180 acaggtccat tctcacacat aagtgccaaa cgcaacagga ggggatacac tagcagcaga     240
ccgttgcaaa cgcaggactc atcctcttct ctaacaccat tttgcatgaa aacagccagt     300
tatgggcttg atggagctcg ctcattccaa ttccttctat taggctacta acaccatgac     360
tttattagcc tgtctatcct ggccccctg gcgaggtcat gtttgtttat ttccgaatgc      420
aacaagctcc gcattacacc cgaacatcac tccagatgag ggctttctga gtgtggggtc     480
aaatagtttc atgttcccaa atggcccaaa actgacagtt taaacgctgt cttggattga     540
cgaatgctca aaaataatct cattaatgct tagcgcagtc tctctatcgc ttctgaaccc     600
ggtggcacct gtgccgaaac gcaaatgggg aaacaacccg cttttttggat gattatgcat   660 tgtcctccac attgtatgct tccaagattc tggtgggaat actgctgata gcctaacgtt     720
catgatcaaa atttaactgt tctaaccct acttggacag gcaatatata aacagaagga     780
agctgccctg tcttaaacct tttttttttat catcattatt agcttacttt cataattgcg    840
actggttcca attgacaagc ttttgatttt aacgactttt aacgacaact tgagaagatc     900
aaaaaacaac taattattcg aaacg                                            925
```